(12) United States Patent
Smets et al.

(10) Patent No.: US 8,551,935 B2
(45) Date of Patent: Oct. 8, 2013

(54) BENEFIT AGENT CONTAINING DELIVERY PARTICLE

(75) Inventors: Johan Smets, Lubbeek (BE); Jiten Odhavji Dihora, Hamilton, OH (US); An Pintens, Brasschaat (BE); Sandra Jacqueline Guinebretiere, Appleton, WI (US); Adam Keith Druckrey, Appleton, WI (US); Peggy Dorothy Sands, Appleton, WI (US); Nianxi Yan, Appleton, WI (US)

(73) Assignee: Appleton Papers Inc., Appleton, WI (US)

( * ) Notice: Subject to any disclaimer, the term of this patent is extended or adjusted under 35 U.S.C. 154(b) by 0 days.

(21) Appl. No.: 13/307,085

(22) Filed: Nov. 30, 2011

(65) Prior Publication Data

US 2012/0071392 A1  Mar. 22, 2012

Related U.S. Application Data

(60) Division of application No. 12/587,840, filed on Oct. 14, 2009, now abandoned, which is a continuation of application No. PCT/US2008/007036, filed on Jun. 4, 2008.

(60) Provisional application No. 60/934,071, filed on Jun. 11, 2007.

(51) Int. Cl.
*C11D 3/50* (2006.01)

(52) U.S. Cl.
USPC .............................................. 512/4; 523/102

(58) Field of Classification Search
USPC .............................................. 512/4; 523/102
See application file for complete search history.

(56) References Cited

U.S. PATENT DOCUMENTS

| | | | |
|---|---|---|---|
| 6,261,483 B1 * | 7/2001 | Frank et al. ................... 264/4.1 |
| 6,391,288 B1 * | 5/2002 | Miyazawa et al. .............. 424/59 |
| 6,719,931 B2 * | 4/2004 | Hoffman et al. ............... 264/4.3 |
| 7,238,655 B2 * | 7/2007 | Ness ................................ 512/4 |
| 2005/0276831 A1 * | 12/2005 | Dihora et al. ................. 424/401 |
| 2006/0248665 A1 * | 11/2006 | Pluyter et al. ..................... 8/406 |
| 2007/0149424 A1 * | 6/2007 | Warr et al. ..................... 510/101 |
| 2007/0202063 A1 * | 8/2007 | Dihora et al. ................. 424/70.1 |
| 2008/0305982 A1 * | 12/2008 | Smets et al. .................. 510/441 |

* cited by examiner

*Primary Examiner* — James J. Seidleck
*Assistant Examiner* — Peter A Salamon
(74) *Attorney, Agent, or Firm* — Benjamin Mieliulis

(57) ABSTRACT

The present invention relates to benefit agent containing delivery particles, compositions comprising said particles, and processes for making and using the aforementioned particles and compositions. When employed in compositions, for example, cleaning or fabric care compositions, such particles increase the efficiency of benefit agent delivery, there by allowing reduced amounts of benefit agents to be employed. In addition to allowing the amount of benefit agent to be reduced, such particles allow a broad range of benefit agents to be employed.

15 Claims, No Drawings

BENEFIT AGENT CONTAINING DELIVERY PARTICLE

CROSS-REFERENCES TO RELATED APPLICATIONS

This application is a divisional application and claims benefit under 35 U.S.C. §120 and §121 of U.S. Ser. No. 12/587,840 filed Oct. 14, 2009, now pending, which is a continuation of and claims benefit under 35 U.S.C. §120 and 365(c) to PCT/US2008/007036 filed Jun. 4, 2008, which claims benefit under 35 U.S.C. §119(e) to U.S. Provisional Application Ser. No. 60/934,071 filed Jun. 11, 2007.

Appleton Papers Inc. and The Procter & Gamble Company executed a joint research agreement on or about Nov. 28, 2005 and this invention was made as a result of activities undertaken within the scope of the joint research agreement between Appleton Papers Inc. and The Procter & Gamble Company that was in effect on or before the date of the invention.

FIELD OF INVENTION

The present application relates to benefit agent containing delivery particles, compositions comprising such particles, and processes for making and using such particles and compositions.

BACKGROUND OF THE INVENTION

Benefit agents, such as perfumes, silicones, waxes, flavors, vitamins and fabric softening agents, are expensive and/or generally less effective when employed at high levels in consumer products, for example, personal care compositions, cleaning compositions, and fabric care compositions. As a result, there is a desire to maximize the effectiveness of such benefit agents. One method of achieving such objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

Accordingly, there is a need for a benefit agent containing delivery particle that provides improved benefit agent delivery efficiency.

SUMMARY OF THE INVENTION

The present invention relates to benefit agent containing delivery particles comprising a core material and a wall material that at least partially surrounds the core material. The present invention also relates to compositions comprising said particles, and processes for making and using such particles and compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the phrase "benefit agent containing delivery particle" encompasses microcapsules including perfume microcapsules.

As used herein, the terms "particle", "benefit agent containing delivery particle", "capsule" and "microcapsule" are synonymous.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefit Agent Delivery Particle

Applicants discovered that the problem of achieving effective and efficient benefit agent delivery can be solved in an economical manner when a benefit agent containing delivery particle, comprising a core material and a wall material that at least partially surrounds said core material and having a certain combination of physical and chemical characteristics is employed. Such physical and chemical characteristics are Fracture Strength, Particle Size, Particle Wall Thickness and Benefit Agent Leakage.

In a first aspect, a benefit agent delivery particles comprising a core material and a shell, said shell at least partially surrounding said core material, is disclosed. As tested in accordance with Applicants test methods, at least 75%, 85% or even 90% of said benefit agent delivery particles have a fracture strength of from about 0.2 MPa to about 10 MPa, from about 0.4 MPa to about 5 MPa, from about 0.6 MPa to about 3.5 MPa, or even from about 0.7 MPa to about 3 MPa; and a benefit agent leakage of from 0% to about 30%, from 0% to about 20%, or even from 0% to about 5%.

In one aspect, at least 75%, 85% or even 90% of said benefit agent delivery particles may have a particle size of from about 1 microns to about 80 microns, about 5 microns to 60 microns, from about 10 microns to about 50 microns, or even from about 15 microns to about 40 microns.

In one aspect, at least 75%, 85% or even 90% of said benefit agent delivery particles may have a particle wall thickness of from about 30 nm to about 250 nm, from about 80 nm to about 180 nm, or even from about 100 nm to about 160 nm.

In one aspect, said benefit agent delivery particles' core material may comprise a material selected from the group consisting of a perfume raw material and/or optionally a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures there of.

In one aspect, said benefit agent delivery particles' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), sigma-Aldrich (St. Louis, Mo. U.S.A.).

In one aspect, said benefit agent delivery particles' core material may comprise a material selected from the group consisting of:
a.) a perfume composition having a Clog P of less than 4.5, less than, 4.25, less than 4.0 or even less than 3.75;
b.) a perfume composition comprising, based on total perfume composition weight, 60% or even 70% perfume materials having a Clog P of less than 4.0;
c.) a perfume composition comprising, based on total perfume composition weight, 35% or 50% or even 60% perfume materials having a Clog P of less than 3.5;
d.) a perfume composition comprising, based on total perfume composition weight, 40% perfume materials having a Clog P of less than 4.0 or even less than 3.5 and at least 1% perfume materials having a Clog P of less than 2.0;
e.) a perfume composition comprising, based on total perfume composition weight, 40% perfume materials having a Clog P of less than 4.0 or even less than 3.5 and at least 15% perfume materials having a Clog P of less than 3.0;
f.) a perfume composition comprising, based on total perfume composition weight, at least 1% or even 2% of a butanoate ester and at least 1% of a pentanoate ester;
g.) a perfume composition comprising, based on total perfume composition weight, at least 2% or even 3% an ester comprising an allyl moiety and at least 10%, 25% or even 30% of another perfume comprising an ester moiety;
h.) a perfume composition comprising, based on total perfume composition weight, at least 1% or even 5% of an aldehyde comprising an alkyl chain moiety;
i.) a perfume composition comprising, based on total perfume composition weight, at least 2% of a butanoate ester;
j.) a perfume composition comprising, based on total perfume composition weight, at least 1% of a pentanoate ester;
k.) a perfume composition comprising, based on total perfume composition weight, at least 3% of an ester comprising an allyl moiety and 1% of an aldehyde comprising an alkyl chain moiety;
l.) a perfume composition comprising, based on total perfume composition weight, at least 25% of a perfume comprising an ester moiety and 1% of an aldehyde comprising an alkyl chain moiety;
m.) a perfume compositions comprising, based on total perfume composition weight, at least 2% or even 10% of a material selected from ionones, like 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimethyl-1-cyclohexen-2-yl)- and mixtures thereof;
n.) a perfume composition comprising, based on total perfume composition weight, at least 0.1% or even 1% of tridec-2-enonitrile, and mandaril, and mixtures thereof;
o.) a perfume composition comprising, based on total perfume composition weight, at least 2% or even 5% of a material selected from 3,7-Dimethyl-6-octene nitrile, 2-cyclohexylidene-2-phenylacetonitrile and mixtures thereof;

p.) a perfume composition comprising, based on total perfume composition weight, at least 80% of one or more perfumes comprising a moiety selected from the group consisting of esters, aldehydes, ionones, nitriles, ketones and combinations thereof;

q.) a perfume composition comprising, based on total perfume composition weight, at least 3% of an ester comprising an allyl moiety; a perfume composition comprising, based on total perfume composition weight, at least 20%, 30% or even 50% of a material selected from the group consisting of: 1-methylethyl-2-methylbutanoate; ethyl-2-methyl pentanoate; 1,5-dimethyl-1-ethenyl-hexyl-4-enyl acetate; p-metnh-1-en-8-yl acetate; 4-(2,6, 6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol,3,7-dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; hexyl ethanoate; 7-acetyl,1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;

r.) a perfume composition comprising, based on total perfume composition weight, at least 20%, 30% or even 50% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones; 1,6-nonadien-3-ol,3,7-dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydroeinnamaldehyde; ethyl-2,4-hexadienoate; 2-propenyl 3-cyclohexanepropanoate; and mixtures thereof;

s.) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;

t.) a perfume composition comprising, based on total perfume composition weight, less than 10% or even 5% perfumes having a Clog P greater than 5.0;

u.) a perfume composition comprising geranyl palmitate; or v.) a perfume composition comprising a first and an optional second material, said first material having:
  (i) a Clog P of at least 2, from about 2 to about 12, from about 2.5 to about 8, or even from about 2.5 to about 6;
  (ii) a boiling point of less than about 280° C., from about 50° C. to about less than about 280° C., from about 50° C. to about less than about 265° C., or even from about 80° C. to about less than about 250° C.; and second optional second material, when present, having
    (i) a Clog P of less than 2.5, or even less than 2 to about 0.1; and
    (ii) a ODT of less than about 100 ppb, from about 0.00001 ppb to about less than about 100 ppb, from about 0.00001 ppb to about less than about 50 ppb or even from about 0.00001 ppb to about less than about 20 ppb.

In one aspect, said benefit agent delivery particles may comprise, based on total benefit agent delivery particle weight, at least 1 weight %, from about 20 to about 95 weight %, from about 50 to about 90 weight %, or even from about 80 to about 85 weight % of a benefit agent.

In one aspect, said benefit agent delivery particles' core material may comprise, based on total core material weight, at least about 20, from about 50 to about 70, or even from about 60 to about 100 wt % benefit agent.

In one aspect, said benefit agent delivery particles may comprise, based on total particle weight, from about 20 weight % to about 95 weight %, from about 50 weight % to about 90 weight %, from about 70 weight % to about 85 weight %, or even from about 80 weight % to about 85 weight % of a perfume composition.

In one aspect, said benefit agent delivery particles may be spray dried said benefit agent delivery particles.

In one aspect, said benefit agent delivery particles may have any combination of the aforementioned parameters as listed in the aforementioned aspects.

Suitable materials for making may be supplied from one or more of the following companies Firmenich (Geneva, Switzerland), Givaudan (Argenteuil, France), IFF (Hazlet, N.J., U.S.A), Quest (Mount Olive, N.J., U.S.A.), Bedoukian (Danbury, Conn., U.S.A.), Sigma Aldrich (St. Louis, Mo., U.S.A.), Millennium Specialty Chemicals (Olympia Fields, Ill., U.S.A.), Polarone International (Jersey City, N.J., U.S.A.), Fragrance Resources (Keyport, N.J., U.S.A.), and Aroma & Flavor Specialties (Danbury, Conn., U.S.A.) or made by following the teachings of Example I of U.S. Pat. No. 5,625,205 and replacing the succinic acid with palmitic acid or Example II of U.S. Pat. No. 5,652,205 and replacing lauroyl chloride with palmitoyl chloride.

Process of Making Benefit Agent Containing Delivery Particles

In one aspect, a process comprising:
- a.) preparing a first solution comprising, based on total solution weight from about 20% to about 90%, from about 40% to about 80%, or even from about 60% to about 80% water, a first emulsifier and a first resin, the ratio of said first emulsifier and said first resin being from about 0.1:0 to about 10:0, from about 0.1:1 to about 10:1, from about 0.5:1 to about 3:1, or even from about 0.8:1 to about 1.1:1;
- b.) preparing a second solution comprising based on total solution weight from about 20% to about 95% water, a second emulsifier and a second resin, the ratio of said second emulsifier and said second resin being from about 0:1 to about 3:1, from about 0.04:1 to about 0.2:1, or even from about 0.05:1 to about 0.15:1;
- c.) combining a core material and said first solution to form a first composition;
- d.) emulsifying said first composition;
- e.) combining said first composition and said second solution to form a second composition and optionally combining any processing aids and said second composition—said first composition and said second solution may be combined in any order but in one aspect said second solution is added to said first composition or said second solution and said first composition are combined simultaneously;
- f.) mixing said second composition for at least 15 minutes, at least 1 hour or even from about 4 hours to about 100 hours at a temperature of from about 25° C. to about 100° C., from about 45° C. to about 90° C., or even from about 50° C. to about 80° C. heat and optionally combining any processing aids to said second composition;
- g.) optionally combining any scavenger material, structurant, and/or anti-agglomeration agent with said second composition during step f.) or thereafter—such materials may be combined in any order but in one aspect the scavenger material is combined first, any structurant second, and then anti-agglomeration agent is combined; and
- h.) optionally spray drying said second composition is disclosed.

In one aspect of the aforementioned process, said core material comprises a perfume raw material.

In one aspect, said benefit agent delivery particles' core material may comprise a material selected from the group consisting of:
- a.) a perfume composition having a Clog P of less than 4.5, less than, 4.25, less than 4.0 or even less than 3.75;
- b.) a perfume composition comprising, based on total perfume composition weight, 60% or even 70% perfume materials having a Clog P of less than 4.0;
- c.) a perfume composition comprising, based on total perfume composition weight, 35% or 50% or even 60% perfume materials having a Clog P of less than 3.5;
- d.) a perfume composition comprising, based on total perfume composition weight, 40% perfume materials having a Clog P of less than 4.0 or even less than 3.5 and at least 1% perfume materials having a Clog P of less than 2.0;
- e.) a perfume composition comprising, based on total perfume composition weight, 40% perfume materials having a Clog P of less than 4.0 or even less than 3.5 and at least 15% perfume materials having a Clog P of less than 3.0;
- f.) a perfume composition comprising, based on total perfume composition weight, at least 1% or even 2% of a butanoate ester and at least 1% of a pentanoate ester;
- g.) a perfume composition comprising, based on total perfume composition weight, at least 2% or even 3% of an ester comprising an allyl moiety and at least 10%, 25% or even 30% of another perfume comprising an ester moiety;
- h.) a perfume composition comprising, based on total perfume composition weight, at least 1% or even 5% of an aldehyde comprising an alkyl chain moiety;
- i.) a perfume composition comprising, based on total perfume composition weight, at least 2% of a butanoate ester;
- j.) a perfume composition comprising, based on total perfume composition weight, at least 1% of a pentanoate ester;
- k.) a perfume composition comprising, based on total perfume composition weight, at least 3% of an ester comprising an allyl moiety and 1% of an aldehyde comprising an alkyl chain moiety;
- l.) a perfume composition comprising, based on total perfume composition weight, at least 25% of a perfume comprising an ester moiety and 1% of an aldehyde comprising an alkyl chain moiety;
- m.) a perfume compositions comprising, based on total perfume composition weight, at least 2% or even 10% of a material selected from ionones, like 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimethyl-1-cyclohexen-2-yl)- and mixtures thereof;
- n.) a perfume composition comprising, based on total perfume composition weight, at least 0.1% or even 1% of tridec-2-enonitrile, and mandaril, and mixtures thereof;
- o.) a perfume composition comprising, based on total perfume composition weight, at least 2% or even 5% of a material selected from 3,7-Dimethyl-6-octene nitrile, 2-cyclohexylidene-2-phenylacetonitrile and mixtures thereof;
- p.) a perfume composition comprising, based on total perfume composition weight, at least 80% of one or more perfumes comprising a moiety selected from the group consisting of esters, aldehydes, ionones, nitriles, ketones and combinations thereof;
- q.) a perfume composition comprising, based on total perfume composition weight, at least 3% of an ester comprising an allyl moiety; a perfume composition comprising, based on total perfume composition weight, at least 20%, 30% or even 50% of a material selected from the group consisting of: 1-methylethyl-2-methylbutanoate;

ethyl-2-methyl pentanoate; 1,5-dimethyl-1-ethenyl-hexyl-4-enyl acetate; p-metnh-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol,3,7-dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; hexyl ethanoate; 7-acetyl,1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-ylpropionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;

r.) a perfume composition comprising, based on total perfume composition weight, at least 20%, 30% or even 50% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones; 1,6-nonadien-3-ol,3,7-dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;

s.) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;

t.) a perfume composition comprising, based on total perfume composition weight, less than 10% or even 5% perfumes having a Clog P greater than 5.0;

u.) a perfume composition comprising geranyl palmitate; or v.) a perfume composition comprising a first and an optional second material, said first material having:
  (i) a Clog P of at least 2, from about 2 to about 12, from about 2.5 to about 8, or even from about 2.5 to about 6;
  (ii) a boiling point of less than about 280° C., from about 50° C. to about less than 280° C., from about 50° C. to about less than about 265° C., or even from about 80° C. to about less than about 250° C.; and second optional second material, when present, having
  (i) a Clog P of less than 2.5, or even less than 2 to about 0.1; and
  (ii) a ODT of less than about 100 ppb, from about 0.00001 ppb to about less than about 100 ppb, from about 0.00001 ppb to about less than about 50 ppb or even from about 0.00001 ppb to about less than about 20 ppb.

In one or more aspects of the process, said first and second resins may comprise the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one or more aspects of the process, said first and second emulsifiers may comprise a moiety selected from the group consisting of carboxy, hydroxyl, thiol, amine, amide and combinations thereof. In one aspect, said emulsifier may have a pKa of less than 5, preferably greater than 0 but less than 5. Emulsifiers include acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), polypropylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

In one or more aspects of the process, said core material may comprise perfume raw material and/or optionally a material selected from the group consisting of a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures there of.

In one or more aspects of the process, the pH of the first and second solutions may be controlled such that the pH of said first and second solution is from about 3.0 to 7.0.

In one or more aspects of the process, during step f.), from about 0% to about 10%, from about 1% to about 5% or even from about 2% to about 4%, based on total second composition weight, of a salt comprising an anion and cation, said anion being selected from the group consisting of chloride, sulfate, phosphate, nitrate, polyphosphate, citrate, maleate, fumarate and mixtures thereof; and said cation being selected from the group consisting of a Periodic Group IA element, Periodic Group IIA element, ammonium cation and mixtures thereof, preferably sodium sulfate, may be combined with said second composition.

In one or more aspects of the process, any of the aforementioned processing parameters may be combined.

Useful structurant materials that may be added to adequately suspend the benefit agent containing delivery particles include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

In one aspect of the invention, benefit agent containing delivery particles are manufactured and are subsequently coated with a material to reduce the rate of leakage of the benefit agent from the particles when the particles are subjected to a bulk environment containing, for example, surfactants, polymers, and solvents. Non-limiting examples of coating materials that can serve as barrier materials include materials selected from the group consisting of pyrrolidone polymers, such as polyvinyl pyrrolidone homopolymer, and its various copolymers with styrene, vinyl acetate, imidazoles, primary and secondary amine containing monomers, polyethyleneimines, including ethoxylated polyethyeleimines, methyl acrylate, polyvinyl acetal; maleic anhydride; polyvinyl alcohol homopolymer, and its various copolymers with vinyl acetate, 2-acrylamide-2-methylpropane sulfonate, primary and secondary amine containing monomers, methyl acrylate; polyacrylamides; polyacrylic acids; polyethyleneimines, ethoxylated polyethyleneimines; microcrystalline waxes; paraffin waxes; modified polysaccharides such as waxy maize or dent corn starch, octenyl succinated starches, derivatized starches such as hydroxyethylated or hydroxypropylated starches, carrageenan, guar gum, pectin, xanthan gum; modified celluloses such as hydrolyzed cellulose acetate, hydroxy propyl cellulose, methyl cellulose, and the like; modified proteins such as gelatin; hydrogenated and non-hydrogenated polyalkenes; fatty acids; hardened shells such as urea crosslinked with formaldehyde, gelatin-polyphosphate, melamine-formaldehyde, polyvinyl alcohol cross-linked with sodium tetraborate or gluteraldehyde; latexes of styrene-butadiene, ethyl cellulose, inorganic materials such as clays including magnesium silicates, aluminosilicates; sodium silicates, and the like; and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A. In one aspect, for example, wherein the particle is employed in a fabric conditioning composition, the coating material comprises sodium silicate. While not being bound by theory, it is believed that sodium silicate's solubility at high pH, but poor solubility at low pH makes it an ideal material for use on particles that may be used in compositions that are formulated at pH below 7 but used in an environment wherein the pH is greater or equal to 7. However, the coating aspect of the present invention is not limited to the benefit agent containing delivery particles of the present invention as any benefit agent containing delivery particle may benefit from the coatings and coating processes disclosed herein.

In one aspect, benefit agent containing delivery particles may be combined with a formaldehyde scavenger. In one aspect, such benefit agent containing delivery particles may comprise the benefit agent containing delivery particles of the present invention. Suitable formaldehyde scavengers include materials selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly (vinyl alcohol)-co-poly(vinyl amine), poly(4-aminostyrene), poly(1-lysine), chitosan, hexane diol, ethylenediamine-N,N'- bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa., U.S.A.

Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent containing delivery particle, said scavengers being combined with said product at a level, based on total product weight, of from about 0.005% to about 0.8%, alternatively from about 0.03% to about 0.5%, alternatively from about 0.065% to about 0.25% of the product formulation.

In another aspect, such formaldehyde scavengers may be combined with a slurry containing said benefit agent containing delivery particle, at a level, based on total slurry weight, of from about 2 wt. % to about 14 wt. %, from about 3.5 wt. % to about 14 wt. % or even from about 5 wt. % to about 14 wt. % and said slurry may be added to a product matrix to which addition an identical or different scavenger may be added at a level, based on total product weight, of from about 0.005% to about 0.5%, alternatively from about 0.01% to about 0.25%, alternatively from about 0.05% to about 0.15% of the product formulation.

In one aspect, one or more of the aforementioned formaldehyde scavengers may be combined with a liquid fabric enhancing product containing a benefit agent containing delivery particle at a level, based on total liquid fabric enhancing product weight, of from 0.005% to about 0.8%, alternatively from about 0.03% to about 0.4%, alternatively from about 0.06% to about 0.25% of the product formulation.

In one aspect, such formaldehyde scavengers may be combined with a consumer product, for example, a liquid laundry detergent product containing a benefit agent containing delivery particle, said scavengers being selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly (oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, from about 0.03 wt. % to about 0.20 wt. % or even from about 0.06 wt. % to about 0.14 wt. %.

In one aspect, such formaldehyde scavengers may be combined with a hair conditioning product containing a benefit agent containing delivery particle, at a level, based on total hair conditioning product weight, of from about 0.003 wt. % to about 0.30 wt. %, from about 0.03 wt. % to about 0.20 wt. % or even from about 0.06 wt. % to about 0.14 wt. %., said selection of scavengers being identical to the list of scavengers in the previous paragraph relating to a liquid laundry detergent product.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Compositions Comprising Benefit Agent Containing Delivery Particles

Applicants' compositions comprise any embodiment of the particle disclosed in the present application—including any embodiment produced by the benefit agent delivery making process detailed in the present specification. In one aspect, said composition is a consumer product. While the precise level of particle that is employed depends on the type and end use of the composition, a composition may comprise from about 0.01 to about 10, from about 0.1 to about 10, or even from about 0.2 to about 5 weight % of said particle based on total composition weight. In one aspect, a consumer product comprising from about 0.001% to about 25%, from about 0.001% to about 10%, or from about 0.01% to about 3%, based on total consumer product mass weight, of the aforementioned benefit agent delivery particles is disclosed.

In one aspect, a cleaning composition comprising from about 0.005% to about 10%, from about 0.01% to about 3%, or from about 0.1% to about 1% based on total cleaning composition mass weight of the aforementioned benefit agent delivery particles is disclosed.

In one aspect, a fabric care composition comprising from about 0.005% to about 10%, from about 0.01% to about 3%, or from about 0.1% to about 1% based on total fabric care mass weight of the aforementioned benefit agent delivery particle composition is disclosed.

In one aspect, when the aforementioned particle composition is employed in a consumer product, for example a liquid consumer product, the particle composition may have a deposition of at least 10%, 20%, 30%, 40%, 50%, 60%, 70%, 80%, 90%, or even 100%.

In one aspect, when the aforementioned particle composition is employed in a consumer product, for example a liquid consumer product, the particle composition may have less than 50%, 40%, 30%, 20%, 10% or even 0% leakage of the encapsulated benefit agent from the microcapsules of said particle composition into said consumer product.

In one aspect, a cleaning composition may comprise, from about 0.1 to about 1 weight % of such particle based on total cleaning composition weight of such particle. In one aspect, a fabric treatment composition may comprise, based on total fabric treatment composition weight, form about 0.01 to about 10% of such particle.

Aspects of the invention include the use of the particles of the present invention in laundry detergent compositions (e.g., TIDET™), hard surface cleaners (e.g., MR CLEAN™), automatic dishwashing liquids (e.g., CASCADE™), dishwashing liquids (e.g., DAWN™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Fabric treatment compositions disclosed herein typically comprise a consumer adjunct material such as a fabric softening active ("FSA"). Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

Consumer Product Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' delivery particles and FSAs. The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonie acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Processes of Making Compositions

The compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

Compositions containing the benefit agent delivery particle disclosed herein can be used to clean or treat a situs inter cilia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

(1) Fracture Strength
  a.) Place 1 gram of particles in 1 liter of distilled deionized (DI) water.
  b.) Permit the particles to remain in the DI water for 10 minutes and then recover the particles by filtration, using a 60 mL syringe filter, 1.2 micron nitrocellulose filter (Millipore, 25 mm diameter).
  c.) Determine the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.
  d.) Use the 50 independent measurements from c.) above, and calculate the percentage of particles having a fracture strength within the claimed range fracture strength range.

(2) ClogP
The "calculated logP" (ClogP) is determined by the fragment approach of Hansch and Leo (cf, A. Leo, in Comprehensive Medicinal Chemistry, Vol. 4, C. Hansch, P. G. Sammens, J. B. Taylor, and C.A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A.

(3) Bodine Point
Boiling point is measured by ASTM method D2887-04a, "Standard Test Method for Boiling Range Distribution of Petroleum Fractions by Gas Chromatography," ASTM International.

(4) Odor Detection Threshold (ODT)
Odour detection threshold is determined using the protocol found in U.S. Pat. No. 6,869,923 B1, from Column 3, line 39 through Column 4, line 15.

(5) Particle Size
  a.) Place 1 gram of particles in 1 liter of distilled deionized (DI) water.
  b.) Permit the particles to remain in the DI water for 10 minutes and then recover the particles by filtration, using a 60 mL syringe filter, 1.2 micron nitrocellulose filter (Millipore, 25 min diameter).

c.) Determine the particle size of 50 individual particles using the experimental apparatus and method of Zhang, Z.; Sun, G; "Mechanical Properties of Melamine-Formaldehyde microcapsules," J. Microencapsulation, vol 18, no. 5, pages 593-602, 2001.

d.) Use the 50 independent measurements from c.) above, and calculate the percentage of particles having a particle size within the claimed range.

(6) Particle Wall Thickness

All references to Leica Microsystems refer to the Company with Corporate Headquarters located at:
Leica Microsystems GmbH
Ernst-Leitz-Strasse 17-37
35578 Wetzlar All references to Drummond refer to the Company located at:
Drummond Scientific Company
Parkway, Box 700
Broomall, Pa. 19008

All references to Hitachi refer to the Company with Corporate Headquarters located at:
Hitachi High Technologies
24-14, Nishi-Shimbashi 1-chome, Minato-ku,
Tokyo 105-8717, Japan All references to Gatan refer to the Company with Corporate Headquarters located at:
Gatan, Inc.
5933 Coronado Lane
Pleasanton, Calif. 94588

All references to Quartz refer to the Company with offices located at:
Quartz Imaging Corporation
Technology Enterprise Facility III
6190 Agronomy Rd, Suite 406
Vancouver, B.C. Canada V6T 1Z3

Materials:
Methylcyclohexane—Alfa Aesar Catalogue Number A16057 or equivalent
Capillary Pipettes—Drummond Catalogue Number 5-000-1005 or equivalent
Flat Specimen Carrier—Leica Microsystems PIN 706897 or equivalent
Copper Washers—Leica Microsystems P/N 706867 or equivalent
Flat Specimen Pod—Leica Microsystems P/N 706839 or equivalent
Loading Device for Flat Specimen Holder—Leica Microsystems P/N 706832 or equivalent
Torque Wrench—Leica Microsystems P/N 870071 or equivalent
Allen Bit, 2 mm Leica Microsystems P/N 870072 or equivalent
Forceps—Leica Microsystems P/N 840105 or equivalent
Gatan Planchette Collet—Gatan P/N PEP5099
Gatan Planchette Specimen Holder—Gatan. P/N PEP1395

Instruments:
Scanning Electron Microscope—Hitachi Model S-5200 SEM/STEM or equivalent
High Pressure Freezer—Leica Microsystems Model 706802 EM Pact or equivalent
Cryotransfer Device—Gatan Model CT3500 or equivalent
Cryotransfer System—Gatan Model CT2500 or equivalent
Gatan ITC Temperature Controller—Gatan Model ITC502 or equivalent Image Analysis Software—Quartz PCI Version 5 or equivalent Sample: Obtain the sample of microcapsules as per the procedure of 1 above entitled "Fracture Strength". 50 samples are required.

Test Procedure

1) Turn on the Leica Microsystems High Pressure Freezer (Leica Microsystems Model Number 706802).
2) Fill up the methylcyclohexane container on the High Pressure Freezer with methylcyclohexane (Alfa Aesar Cat. # A16057 or equivalent).
3) Fill up the liquid nitrogen dewar on the High Pressure Freezer.
4) Fill the liquid nitrogen bath on the High Pressure Freezer.
5) The display on the High Pressure Freezer will show Load Sample on the front panel when the instrument is ready to use.
6) Start the Hitachi Model S-5200 SEM/STEM and set the Accelerating Voltage to 3.0 KV and the Emission Current to 20 μA.
7) Fill the Anti-contaminator Dewar located on the lower right side of the Hitachi Model 5-5200 SEM/STEM microscope column with liquid nitrogen.
8) Fill the liquid nitrogen dewar on the Gatan Alto 2500 Cryotransfer System (Galan Model CT2500). Replenish the liquid nitrogen until the dewar remains full. The device is ready to use when the prepchamber temperature reads below −190° C.
9) Place a copper washer (Leica Microsystems P/N 706867) on top of the flat specimen carrier such that the hole in the washer aligns with the well in the flat specimen carrier.
10) Take a glass capillary pipette (Drummond P/N 5-000-1005 or similar) and insert the provided wire plunger into one end of the pipette.
11) Insert the pipette into the microcapsule dispersion and withdraw the plunger part way to pull a few microliters of the dispersion into the pipette.
12) Place the tip of the pipette in the well in the flat specimen carrier and push the plunger into the pipette to dispense a small amount of liquid until the well is just slightly overfilled.
13) Insert a 2 mm Allen key bit (Leica Microsystems P/N 870072) into the torque wrench (Leica Microsystems P/N 870071).
14) Using the torque wrench with the bit, loosen the Diamond Locking Screw in the Flat Specimen Pod (Leica Microsystems P/N 706839).
15) Place the Flat Specimen Holder and Copper Washer into the Flat Specimen Pod.
16) Use the torque wrench with the 2 mm Allen key bit to tighten the Diamond Locking Screw in the Flat Specimen Pod onto the specimen until the torque wrench clicks twice.
17) Attach the Loading Device for the Flat Specimen Holder (Leica Microsystems P/N 706832) to the Flat Specimen Pod by screwing it onto the exposed threads of the Diamond Locking Screw.
18) Place the Loading Device for the Flat Specimen Holder with the Flat Specimen Pod onto the EM Pact High Pressure Freezer (Leica Microsystems P/N 706802) and insert it into the High Pressure Freezer.
19) Freeze the specimen using the High Pressure Freezer.
20) Transfer the Flat Specimen Pod to the Unloading Station and unscrew the Loading Device for the Flat Specimen Carrier being careful to keep it immersed in the liquid nitrogen bath.
21) Using the torque wrench, loosen the Diamond Locking Screw.

22) Using tweezers with the tips cooled in liquid nitrogen until the liquid nitrogen stops boiling, remove the Flat Specimen Carrier from the Flat Specimen Pod and place it into a small container in the liquid nitrogen bath.
23) Place the Gatan CT3500 Cryotransfer Device (Gatan Model Number CT3500) into the Gatan Specimen Workstation.
24) Fill the liquid nitrogen dewar on the Gatan CT3500 Cryotransfer device and fill the dewar on the Gatan Specimen Workstation replenishing the liquid nitrogen as necessary until rapid boiling of the liquid nitrogen stops.
25) Transfer the Flat Specimen Holder to the Gatan Specimen Workstation while keeping it in a container of liquid nitrogen.
26) Using tweezers cooled in liquid nitrogen until the liquid nitrogen stops boiling, place the flat specimen holder into the Gatan Planchette Collet (Gatan P/N PEP5099) and press down firmly.
27) Place the assembly from step 26 into the Gatan Planchette Specimen Holder (Gatan P/N PEP1395) and press down firmly.
28) Push the Gatan Cryotransfer device back into the Gatan Specimen Workstation.
29) Using the Gatan supplied 5 mm Friction Tool, screw the Gatan Planchette Specimen Holder into the Gatan Cryotransfer device.
30) Remove the Gatan Cryotransfer device from the Gatan Specimen Workstation and insert it into the Gatan Alto 2500 Cryotransfer System.
31) Attach the Gatan ITC Temperature Controller (Gatan Model Number ITC502) to the Gatan Cryotransfer device by attaching the Temperature Measurement Lead from the Gatan ITC controller to the connector on top of the Gatan Ciyotransfer device.
32) Using the Gatan ITC Controller, raise the temperature of the specimen to −120° C.
33) Using the fracturing knife, break off the copper washer to fracture the specimen.
34) Reduce the temperature of the specimen below −160° C.
35) With the voltage set to 6 KV and the gas flow set to provide 10 mA sputter current, press the sputter button and once the current displays 10 mA, let the coater run for 60-90 seconds coating the specimen with gold/palladium.
36) Close the frost shield on the Gatan CT3500 Cryotransfer Device and transfer the specimen to the Hitachi S-5200 SEM/STEM.
37) Wait for the temperature of the Gatan CT3500 Cryotransfer device to stabilize, typically between −170° C. and −172° C.
38) Open the frost shield on the Gatan CT3500 Cryotransfer device by turning the frost shield control knob counterclockwise.
39) Move the sample around using the stage control trackball, locate a broken microcapsule and adjust the magnification to 50,000 to 150,000×.
40) Adjust the focus and stigmation controls to obtain the best image.
41) Acquire an image of the cross-section of the capsule wall.
Calculations
1) Select the ruler tool in the Quartz PCI software.
2) Move the cursor to one edge of the microcapsule wall.
3) Click and hold the left mouse button while dragging the mouse cursor to the opposite side of the capsule wall keeping the drawn line perpendicular to the face of the capsule wall to measure the wall thickness.
4) Use 50 independent measurements (1 measurement for each capsule) to calculate the percentage of particles having a wall thickness in the claimed range.

(7) Benefit Agent Leakage
a.) Obtain 2, one gram samples of benefit agent particle composition.
b.) Add 1 gram (Sample 1) of particle composition to 99 grams of product matrix that the particle will be employed in and with the second sample immediately proceed to Step d below.
c.) Age the particle containing product matrix (Sample 1) of a.) above for 2 weeks at 35° C. in a sealed, glass jar.
d.) Recover the particle composition's particles from the product matrix of c.) (Sample 1 in product matrix) and from particle composition (Sample 2) above by filtration.
e.) Treat each particle sample from d.) above with a solvent that will extract all the benefit agent from each samples' particles.
f.) Inject the benefit agent containing solvent from each sample from e.) above into a Gas Chromatograph and integrate the peak areas to determine the total quantity of benefit agent extracted from each sample.
g.) The benefit agent leakage is defined as:
Value from f.) above for Sample 2—Value from 1.) above for Sample 1.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

84 wt % Core/16 wt % Wall Melamine Formaldehyde (MF) Capsule 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 AccusiZer.

Example 2

80 wt % Core/20 wt % Wall Melamine Formaldehyde Capsule 18 grams of a blend of 50% butyl acrylate-acrylic acid copolymer emulsifier (Colloid C351, 25% solids, pka 4.5-4.7, Kemira) and 50% polyacrylic acid (35% solids, pKa 1.5-2.5, Aldrich) is dissolved and mixed in 200 grams deionized water. The pH of the solution is adjusted to pH of 3.5 with sodium hydroxide solution. 6.5 grams of partially methylated methylol melamine resin (Cymel 385, 80% solids Cytec) is added to the emulsifier solution. 200 grams of perfume oil is added to the previous mixture under mechanical agitation and the temperature is raised to 60° C. After mixing at higher speed until a stable emulsion is obtained, the second solution and 3.5 grams of sodium sulfate salt are poured into the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.6, 30 grams of partially methylated methylol melamine resin (Cymel 385, 80% Cytec). This mixture is heated to 75° C. and maintained 6 hours with continuous stirring to complete the encapsulation process. 23 grams of acetoacetamide (Sigma-Aldrich, Saint Louis, Mo., U.S.A.) is added to the suspension.

Example 3

80 wt % Core/20 wt % Melamine Formaldehyde Wall Capsule 36 grams of butyl acrylate-acrylic acid copolymer emulsifier (Colloid C351, 25% solids, pKa 4.5-4.7, Kemira) is dissolved and mixed in 200 grams deionized water. The pH of the solution is adjusted to pH of 5.0 with sodium hydroxide solution. 12 grams of partially methylated methylol melamine resin (Cymel 385, 80% solids, Cytec) is added to the emulsifier solution. 200 grams of perfume oil is added to the previous mixture under mechanical agitation and the temperature is raised to 65° C. After mixing at higher speed until a stable emulsion is obtained, the second solution and 5 grams of sodium sulfate salt are added to the emulsion. This second solution contains 12 grams of butyl acrylate-acrylic acid copolymer emulsifier (Colloid C351, 25% solids, pKa 4.5-4.7, Kemira), 120 grams of distilled water, sodium hydroxide solution to adjust pH to 5, 33 grams of partially methylated methylol melamine resin (Cymel 385, 80% solids, Cytec). This mixture is heated to 65° C. and maintained overnight with continuous stirring to complete the encapsulation process. 23 grams of acetoacetamide (Sigma-Aldrich, Saint Louis, Mo., U.S.A.) is added to the suspension.

Example 4

80 wt % Core/20 wt % Wall Melamine Formaldehyde Capsule 20 grams of butyl acrylate-acrylic acid copolymer emulsifier (Colloid C351, 25% solids, pKa 4.5-4.7, Kemira) is dissolved and mixed in 200 grams deionized water. The pH of the solution is adjusted to pH of 5.5 with sodium hydroxide solution. 6 grams of partially methylated methylol melamine resin (Cymel 385, 80% solids, Cytec) is added to the emulsifier solution. 200 grams of perfume oil is added to the previous mixture under mechanical agitation and the temperature is raised to 55° C. After mixing at higher speed until a stable emulsion is obtained, the second solution and 9 grams of sodium sulfate salt is added to the emulsion. This second solution contains 8 grams of polyacrylic acid (35% solids, pka 1.5-2.5, Aldrich), 120 grams of distilled water, sodium hydroxide solution to adjust pH to 4.4, 35 grams of partially methylated methylol melamine resin (Cymel 385, 80% solids, Cytec). This mixture is heated to 80° C. and maintained 4 hours with continuous stirring to complete the encapsulation process. 23 grams of acetoacetamide (Sigma-Aldrich, Saint Louis, Mo., U.S.A.) is added to the suspension.

Example 5

Melamine Formaldehyde Capsule

The composition of and the procedures for preparing the capsules are the same composition as in Example 4 except for the following: the melamine formaldehyde resin is a mix of 80% partially methylated methylol melamine resin and 20% of fully methylated melamine resin.

Example 6

Melamine Formaldehyde Capsule

The procedure for preparing the capsules is the same as in Example 4, except for the following compositional changes to the perfume emulsification liquor (the first solution):

| Material | A | B | C | D | E | F | G |
|---|---|---|---|---|---|---|---|
| Copolymer of Polyacrylic Acid-Butyl Acrylate | 42 | 31 | 0 | 20 | 26 | 18 | 0 |
| Polyacrylic Acid | 0 | 21 | 29 | 14 | 0 | 22 | 27 |
| 20% NaOH | 2 | 3 | 6 | 9 | 2 | 7 | 7 |
| Melamine Resin | 19 | 21 | 21 | 8 | 4 | 7 | 17 |
| Perfume Oil | 265 | 290 | 246 | 224 | 220 | 200 | 204 |
| Water | 95 | 104 | 103 | 225 | 159 | 189 | 237 |

The procedure for preparing the capsules is the same as in Example 4, except for the following compositional changes to the second solution:

| Material | A | B | C | D | E | F | G |
|---|---|---|---|---|---|---|---|
| Copolymer of Polyacrylic Acid-Butyl Acrylate | 11 | 0 | 15 | 0 | 0 | 3 | 3 |
| Polyacrylic Acid | 11 | 12 | 0 | 4 | 9 | 8 | 10 |
| 20% NaOH | 0.4 | 0.4 | 0.1 | 0.3 | 0.4 | 0.4 | 0.4 |
| Melamine Resin | 8 | 4 | 16 | 13 | 26 | 23 | 29 |
| Water | 115 | 126 | 43 | 147 | 52 | 47 | 78 |

Followed by the addition of acetoacetamide at a level of 5 wt % of the weight of the batch.

Example 7

Melamine Formaldehyde Capsule

The composition of and the procedures for preparing the capsules are the same composition as in Example 4 except for the following: 0.7% of ammonium hydroxide is added to the suspension instead of acetoacetamide.

Example 8

Production of Spray Dried Microcapsule 1200 g of perfume microcapsule slurry, containing one or more of the variants of microcapsules disclosed in the present specification, is mixed together with 700 g of water for 10 minutes using an IKA Eurostar mixer with R1382 attachment at a speed of 180 rpm. The mixture is then transferred over to a feeding vessel to be spray dried in a 1.2 m diameter Niro Production Minor. The slurry is fed into the tower using a Watson-Marlow 504U peristaltic pump and atomised using a 100 mm diameter rotary atomiser run at 18000 rpm, with co-current air flow for drying. The shiny is dried using an inlet temperature of 200° C. and outlet temperature of 95° C. to form a fine powder. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 9

Non-limiting examples of product formulations containing microcapsules summarized in the following table.

| (% wt) | A | B | C | D | E | F | G | H | I | J |
|---|---|---|---|---|---|---|---|---|---|---|
| FSA [a] | 14 | 16.47 | 14 | 12 | 12 | 16.47 | — | — | 5 | 5 |
| FSA [b] | — | — | — | — | — | — | 3.00 | — | — | — |
| FSA [c] | — | — | — | — | — | — | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Microcapsule (% active) * | 0.6 | 0.75 | 0.6 | 0.75 | 0.37 | 0.60 | 0.37 | 0.6 | 0.37 | 0.37 |
| Formaldehyde Scavenger [e] | 0.40 | 0.13 | 0.065 | 0.25 | 0.03 | 0.030 | 0.030 | 0.065 | 0.03 | 0.03 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[e] The formaldehyde scavenger is acetoacetamide available from Aldrich.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the tradename DC2310.
[l] Hydrophobically-modified ethoxylated urethane available from Rohm and Haas under the tradename Aculan 44.
* Suitable combinations of the microcapsules provided in Examples 1 through 8. (Percent active relates to the core content of the microcapsule.)
† balance

Example 10

Microcapsules in Dry Laundry Formulations

|  | % w/w granular laundry detergent composition | | | | | | |
|---|---|---|---|---|---|---|---|
| Component | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules* | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*Microcapsule added as 35% active slurry. Core/wall ratio can range from 80/20 up to 90/10 and average particle diameter can range from 5 μm to 50 μm

Example 11

Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |

-continued

| Ingredient | HDL 1 | HDL 2 | HDL3 | HDL4 | HDL 5 | HDL 6 |
|---|---|---|---|---|---|---|
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules* | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

*Perfume Microcapsules Slurry in accordance with the teaching of the present specification.

Example 12

Urea Formaldehyde Capsule

Into a mixture of 89.5 grams of water, 5 grams of urea, 0.5 gram of resorcinol and 5 grams of an alkyl acrylate-acrylic acid copolymer, adjusted to pH 4.0, were emulsified 90 grams of perfume oil. These mixtures were emulsified and the resulting mixture is placed in a container which is mounted in a room temperature water bath, continuous stirring is provided, 13.5 grams of 37% formaldehyde solution were added and the bath is heated to 55° C. and maintained at that temperature overnight to initiate and complete encapsulation.

Example 13

The perfume microcapsules of Examples 1-7 are tested in accordance with the test methods of the present invention are found to have a fracture strengths of from about 0.2 MPa to about 10 MPa, from about 0.4 MPa to about 5 MPa, from about 0.6 MPa to about 3.5 MPa, and even from about 0.7 MPa to about 3 MPa; a benefit agent leakage of from 0% to about 30%, from 0% to about 20%, and even from about 0% to about 5%; a particle size of from about 1 microns to about 80 microns, about 5 microns to 60 microns, from about 10 microns to about 50 microns, and even from about 15 microns to about 40 microns; and a particle wall thickness of from about 60 nm to about 250 nm, from about 80 nm to about 180 nm, or even from about 100 nm to about 160 nm.

Example 12

| | Examples of liquid detergents | | | |
|---|---|---|---|---|
| | A | B | C | D |
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | | |
| Silicone emulsion | 0.0030 | 0.0030 | 0.0030 | 0.0030 |
| Dye | 0.002 | 0.002 | 0.002 | 0.002 |
| Opacifier (Styrene Acrylate based) | | | | |
| Bentonite Softening Clay | | | | |
| Acrylamide/MAPTAC (ex Nalco Chemicals of Naperville, IL) | | | 0.40 | 0.40 |
| Mirapol 550 (ex Rhodia Chemie, France) | | | | |
| Polyquaternium 10 - Cationic hydroxyl ethyl cellulose | | | | |
| PP-5495 (silicone ex Dow Corning Corporation, Midland, MI) | | | | |
| DC 1664 (silicone ex Dow Corning Corporation, Midland, MI) | | | | |

-continued

| Examples of liquid detergents | A | B | C | D |
|---|---|---|---|---|
| Pearlescent agent* | | | | 0.2 |
| Perfume micro capsules (expressed as perfume oil) | 0.8 | 0.5 | 1.0 | 0.7 |
| Perfume | 0.7 | 0.55 | 1.00 | 1.00 |
| Poly Ethylene Imine MW 25000 | | | | |
| Water | Up to 100 | Up to 100 | Up to 100 | Up to 100 |

*Mica-TiO2 (Prestige Silk Silver Star ex Eckart) or BiOCl (Biron Silver CO-Merck) or pre-crystallized EGDS (Tegopearl N 100 ex Degussa, expressed as pure EGDS)

| Examples of liquid detergents | E | F | G | H |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | |
| C12-C14 alkyl poly ethoxylate (3) sulfate Na salt | 10.60 | 6.78 | 10.60 | 10.60 |
| Linear Alkylbenzene sulfonate acid | 0.79 | 1.19 | 0.79 | 0.79 |
| Citric Acid | 3.75 | 2.40 | 3.75 | 3.75 |
| C12-C18 Fatty Acid | 7.02 | 4.48 | 7.02 | 7.02 |
| Enzymes | 0.60 | 1.0 | 0.60 | |
| Boric Acid | 1.25 | 1.25 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.14 | 0.06 | 0.14 | |
| Hydrogenated Castor Oil | 0.20 | 0.300 | 0.20 | 0.20 |
| Ethanol | 2.50 | 1.00 | 2.50 | 2.50 |
| 1,2 propanediol | 1.14 | 0.09 | 1.14 | 1.14 |
| Sodium hydroxide | 4.60 | 3.01 | 4.60 | 4.60 |
| Mono Ethanol Amine | | | | |
| Na Cumene Sulphonate | | | | |
| Silicone emulsion | 0.0030 | 0.0030 | 0.0030 | 0.0030 |
| Dye | 0.002 | 0.00084 | 0.00084 | 0.00084 |
| Opacifier (Styrene Acrylate based) | | | | 0.1 |
| Bentonite Softening Clay | | | | |
| Acrylamide/MAPTAC (ex Nalco Chemicals of Naperville, IL) | | | 0.40 | |
| Mirapol 550 (ex Rhodia Chemie, France) | 0.40 | 0.25 | | |
| Polyquaternium 10 - Cationic hydroxyl ethyl cellulose | | | | 0.30 |
| PP-5495 (silicone ex Dow Corning Corporation, Midland, MI) | | 3.0 | | |
| DC 1664 (silicone ex Dow Corning Corporation, Midland, MI) | 3.0 | | 3.0 | |
| Pearlescent agent * | | | 0.2 | |
| Perfume micro capsules (expressed as perfume oil) | 0.9 | 0.3 | 0.5 | 1.2 |
| Perfume | 1.00 | .65 | 1.00 | 1.00 |
| Poly Ethylene Imine MW 25000 | | | | |
| Water | Up to 100 | Up to 100 | Up to 100 | Up to 100 |

| Examples of liquid detergents | I | J | K |
|---|---|---|---|
| C14-C15 alkyl poly ethoxylate (8) | 4.00 | 6.1 | |
| C12-C14 alkyl poly ethoxylate (7) | | | 2.00 |
| C12-C14 alkyl poly ethoxylate (3) sulfate Na salt | 6.78 | | |
| Linear Alkylbenzene sulfonate acid | 1.19 | 7.8 | 15.0 |
| Citric Acid | 2.40 | 2.6 | 2.50 |
| C12-C18 Fatty Acid | 4.48 | 2.6 | 11.4 |
| Enzymes | | .55 | .07 |
| Boric Acid | 1.25 | 1.50 | 1.3 |
| Trans-sulphated ethoxylated hexamethylene diamine quat | 0.71 | 1.20 | |
| Diethylene triamine penta methylene phosphonic acid | 0.11 | 0.20 | 0.7 |
| Fluorescent brightener | | 0.09 | 0.14 |
| Hydrogenated Castor Oil | 0.300 | 0.45 | 0.09 |
| Ethanol | 1.00 | 1.40 | 0.7 |
| 1,2 propanediol | 0.09 | 3.30 | 6.7 |
| Sodium hydroxide | 3.01 | 3.00 | 5.5 |
| Mono Ethanol Amine | | 0.50 | |
| Na Cumene Sulphonate | | | 1.6 |
| Silicone emulsion | 0.0030 | 0.0030 | 0.30 |
| Dye | 0.00084 | 0.02 | 0.004 |
| Opacifier (Styrene Acrylate based) | | | |
| Bentonite Softening Clay | | | 3.40 |
| Acrylamide/MAPTAC (ex Nalco Chemicals of Naperville, IL) | | | |
| Mirapol 550 (ex Rhodia Chemie, France) | | | |
| Polyquaternium 10 - Cationic hydroxyl ethyl cellulose | 0.18 | | |
| PP-5495 (silicone ex Dow Corning Corporation, Midland, MI) | | | |
| DC 1664 (silicone ex Dow Corning Corporation, Midland, MI) | 3.0 | | |
| Pearlescent agent * | | 0.2 | |
| Perfume micro capsules (expressed as perfume oil) | 0.2 | 0.45 | 0.75 |
| Perfume | 0.65 | 0.5 | 1.0 |
| Poly Ethylene Imine MW 25000 | | | 0.08 |
| Water | Up to 100 | Up to 100 | Up to 100 |

| Examples of liquid detergents | L | M** | N |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules (expressed as perfume oil) | 1.6 | 1.5 | 1.4 |
| Perfume | 1.2 | 1.6 | 1.0 |
| Form. Phenyl Boronic Acid | | | Present |
| Water | Up to 100 | Up to 100 | Up to 100 |

**Low water liquid detergent in Polyvinyl alcohol unidose/sachet

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of producing a benefit agent delivery particle, said method comprising the steps of:
   a.) preparing a first solution comprising, a first emulsifier and a first resin, and based on the total first solution weight, the first emulsifier and the first resin comprise from about 20% to about 90% of the first solution wherein the ratio of said first emulsifier and said first resin is from about 0.1:1 to about 10:1;
   b.) preparing a second solution comprising based on total solution weight from about 20% to about 95% water, a second emulsifier and a second resin, the ratio of said second emulsifier and said second resin being from about 0:1 to about 3:1;
   c.) combining a core material and said first solution to form a first composition;
   d.) emulsifying said first composition;
   e.) combining said first composition and said second solution to form a second composition, and optionally combining any processing aids to said second composition;
   f.) mixing said second composition at a temperature of from about 25° C. to about 100° C. for a time sufficient to form said benefit agent delivery particle, and optionally combining any processing aids to said second composition;
   g.) optionally combining any scavenger material, structurant, and/or anti-agglomeration agent with said second composition during step f.) or thereafter
   h.) optionally spray drying said second composition containing said benefit agent delivery particles,
   wherein said emulsifier is selected from acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

2. The method according to claim 1, wherein said benefit agent delivery particle has core material which comprises a perfume raw material.

3. The method according to claim 1, wherein said core material comprises:
   a.) a perfume composition having a Clog P of less than 4.5;
   b.) a perfume composition comprising, based on total perfume composition weight, 60% perfume materials having a Clog P of less than 4.0;
   c.) a perfume composition comprising, based on total perfume composition weight, 35% perfume materials having a Clog P of less than 3.5;
   d.) a perfume composition comprising, based on total perfume composition weight, 40% perfume materials having a Clog P of less than 4.0 and at least 1% perfume materials having a Clog P of less than 2.0;
   e.) a perfume composition comprising, based on total perfume composition weight, 40% perfume materials having a Clog P of less than 4.0 and at least 15% perfume materials having a Clog P of less than 3.0;
   f.) a perfume composition comprising, based on total perfume composition weight, at least 1% of a butanoate ester and at least 1% of a pentanoate ester;
   g.) a perfume composition comprising, based on total perfume composition weight, at least 2% of an ester comprising an allyl moiety and at least 10% of another perfume comprising an ester moiety;
   h.) a perfume composition comprising, based on total perfume composition weight, at least 1% of an aldehyde comprising an alkyl chain moiety;
   i.) a perfume composition comprising, based on total perfume composition weight, at least 2% of a butanoate ester;
   j.) a perfume composition comprising, based on total perfume composition weight, at least 1% of a pentanoate ester;
   k.) a perfume composition comprising, based on total perfume composition weight, at least 3% of an ester comprising an allyl moiety and 1% of an aldehyde comprising an alkyl chain moiety;
   l.) a perfume composition comprising, based on total perfume composition weight, at least 25% of a perfume comprising an ester moiety and 1% of an aldehyde comprising an alkyl chain moiety;
   m.) a perfume composition comprising, based on total perfume composition weight, at least 2% of a material selected from ionones, preferably 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimethyl-1-cyclohexen-2-yl)- and mixtures thereof;
   n.) a perfume composition comprising, based on total perfume composition weight, at least 0.1% of tridec-2-enonitrile, and mandaril, and mixtures thereof;
   o.) a perfume composition comprising, based on total perfume composition weight, at least 2% of a material selected from 3,7-Dimethyl-6-octene nitrile, 2-cyclohexylidene-2-phenylacetonitrile and mixtures thereof;
   p.) a perfume composition comprising, based on total perfume composition weight, at least 80% of one or more perfumes comprising a moiety selected from the group consisting of esters, aldehydes, ionones, nitriles, ketones and combinations thereof;
   q.) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhexyl-4-enyl acetate; p-metnh-1-en-8-ylacetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol,3,7-dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitril; patchouli oil; ethyl tricycle[5.2.1.0]decan-2-carboxylate; 2,2-dimethyl-cyclohexanepropanol; hexyl ethanoate; 7-acetyl,1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-a; 1-decyl aldehyde; 1-octanal; 4-t-butyl-α-methylhydrocinnamaldehyde; alpha-hexylcinnamaldehyde; ethyl-2,4-hexadienoate; 2-propenyl 3-cyclohexanepropanoate; and mixtures thereof;

r.) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo[2.2.1]heptan-2-ol; 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones; 1,6-nonadien-3-ol,3,7-dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle[5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl-α-methylhydrocinnamaldehyde; ethyl-2,4-hexadienoate; 2-propenyl 3-cyclohexanepropanoate; and mixtures thereof;

s.) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof;

t.) a perfume composition comprising, based on total perfume composition weight, less than 10% a perfume having a Clog P greater than 5.0;

u.) a perfume composition comprising geranyl palmitate; or v.) a perfume composition comprising a first and an optional second material, said first material having:
(i) a Clog P of at least 2;
(ii) a boiling point of less than about 280° C.; and second optional second material, when present, having
(i) a Clog P of less than 2.5; and
(ii) a ODT of less than about 100 ppb.

4. The method according to claim 1, wherein said resin material comprises a reaction product of an aldehyde with an amine.

5. The composition of claim 4, wherein said aldehyde comprises formaldehyde, and said amine comprises melamine, urea, benzoguanamine, glycoluril, or mixtures thereof.

6. The method of claim 5, wherein said melamine comprises methylol melamine, methylated methylol melamine, imino melamine or mixtures thereof.

7. The method of claim 5, wherein said urea comprises dimethylol urea, methylated dimethylol urea, urea-resorcinol, or mixtures thereof.

8. The method according to claim 1 wherein said emulsifier comprises a moiety selected from the group consisting of carboxy, hydroxyl, thiol, amine, amide and combinations thereof, said emulsifier having a pKa of less than 5.

9. The method according to claim 8, wherein said pKa is greater than 0 but less than 5.

10. The method according to claim 1, wherein said core material comprises a material selected from the group consisting of vegetable oil, esters of vegetable oils, esters, straight or branched chain hydrocarbons, partially hydrogenated terphenyls, dialkyl phthalates, alkyl biphenyls, alkylated naphthalene, petroleum spirits, aromatic solvents, silicone oils, or mixtures thereof.

11. The method according to claim 1, wherein said core material is selected from caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof, dibutyl adipate, dibutyl phthalate, butyl benzyl adipate, benzyl octyl adipate, tricresyl phosphate, trioctyl phosphate and mixtures thereof, straight or branched chain hydrocarbons having a boiling point of greater than about 80° C., monoisopropylbiphenyl, dipropylnaphthalene, kerosene, mineral oil, benzene, and toluene.

12. The method according to claim 1, wherein in any of the process steps, the pH of the first and second solutions is controlled such that the pH of said first and second solution is from about 3.0 to 7.0.

13. The method according to claim 1, wherein in step f.), from about 0% to about 10%, based on total second composition weight, of a salt comprising an anion and cation, is combined with said second composition.

14. The method according to claim 13, wherein said anion is selected from the group consisting of chloride, sulfate, phosphate, nitrate, polyphosphate, citrate, maleate, fumarate and mixtures thereof; and said cation is selected from the group consisting of a Periodic Group IA element, Periodic Group IIA element, ammonium cation and mixtures thereof.

15. The method according to claim 13, wherein from about 1% to 5% of said salt is present.

* * * * *